US00PP33219P2

(12) United States Plant Patent
Snijder

(10) Patent No.: US PP33,219 P2
(45) Date of Patent: Jun. 29, 2021

(54) ***PELARGONIUM* PLANT NAMED 'PECZ0021'**

(50) Latin Name: ***Pelargonium* interspecific**
Varietal Denomination: PECZ0021

(71) Applicant: SYNGENTA CROP PROTECTION AG, Basel (CH)

(72) Inventor: Ronald Christiaan Snijder, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/910,111

(22) Filed: Jun. 24, 2020

(51) Int. Cl.
*A01H 5/02* (2018.01)
*A01H 6/42* (2018.01)

(52) U.S. Cl.
USPC ..... Plt./324
CPC ..... *A01H 6/425* (2018.05); *A01H 5/02* (2013.01)

(58) Field of Classification Search
USPC ..... Plt./324
See application file for complete search history.

*Primary Examiner* — Susan McCormick Ewoldt
(74) *Attorney, Agent, or Firm* — Dale Skalla

(57) ABSTRACT

A new *Pelargonium* plant named 'PECZ0021' particularly distinguished dark red-purple colored inflorescences with large semi-double bicolored florets with a large dark red spot on each petal, held above dark green foliage, on a vigorous mounding plant.

1 Drawing Sheet

Latin name of the genus and species of the plant claimed: *Pelargonium* interspecific.

Varietal denomination: 'PECZ0021'.

BACKGROUND OF THE NEW PLANT

The present invention comprises a new *Pelargonium*, botanically known as *Pelargonium* interspecific, and hereinafter referred to by the variety name 'PECZ0021'.

'PECZ0021' is a product of a planned breeding program. The new cultivar 'PECZ0021' has dark red-purple colored inflorescences with large semi-double bicolored florets with a large dark red spot on each petal, held above dark green foliage, on a vigorous mounding plant.

'PECZ0021' originates from a hybridization in a controlled breeding program made in July 2015, in a greenhouse in Enkhuizen, The Netherlands. The female parent was a unpatented plant of *P.* interspecific parentage identified as '11339-4' with lighter green foliage and more lavender colored florets and larger plant habit when compared to 'PECZ0021'.

The male parent of 'PECZ0021' was an unpatented, proprietary plant of *P.* x *hortorum* parentage, identified as 'PEZ-AZ3257-03' with single florets and a more compact plant habit when compared to 'PECZ0021'. The resultant seed was sown in December 2015.

'PECZ0021' was selected as one flowering plant within the progeny of the stated cross in May 2016 in a greenhouse in Enkhuizen, The Netherlands.

The first act of asexual reproduction of 'PECZ0021' was accomplished when vegetative cuttings were propagated from the initial selection in the April 2016 in a greenhouse in Enkhuizen, The Netherlands.

BRIEF SUMMARY OF INVENTION

Horticultural examination of plants grown from cuttings of the plant initiated in April 2016 in Enkhuizen, The Netherlands and continuing thereafter, has demonstrated that the combination of characteristics as herein disclosed for 'PECZ0021' are firmly fixed and are retained through successive generations of asexual reproduction.

'PECZ0021' has not been observed under all possible environmental conditions. The phenotype may vary significantly with variations in environment such as temperature, light intensity, and day length.

A Plant Breeder's Right for this cultivar has not yet been applied for. 'PECZ0021' has not been made publicly available prior to the effective filing date of this application, notwithstanding any disclosure that may have been made less than one year prior to the effective filing date of this application by the inventor or another who obtained 'PECZ0021' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PECZ0021' with colors being as true as possible with an illustration of this type.

Figure 1:
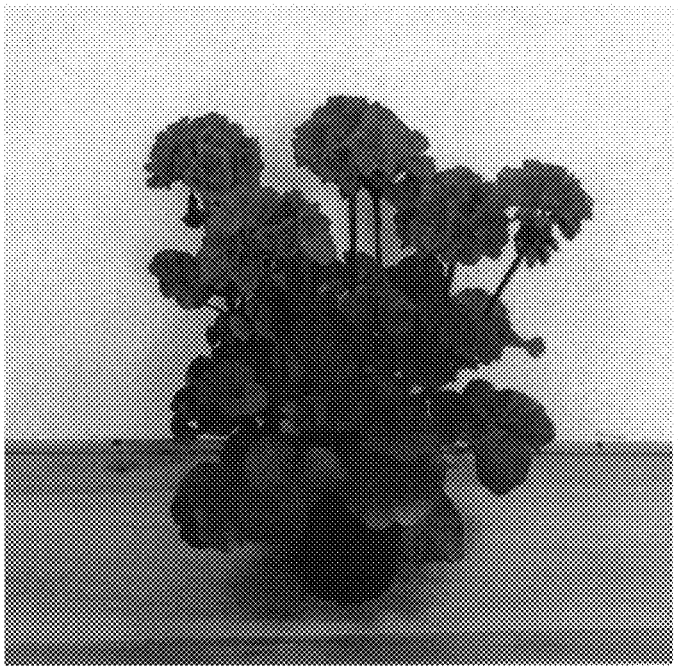
Figure 2:
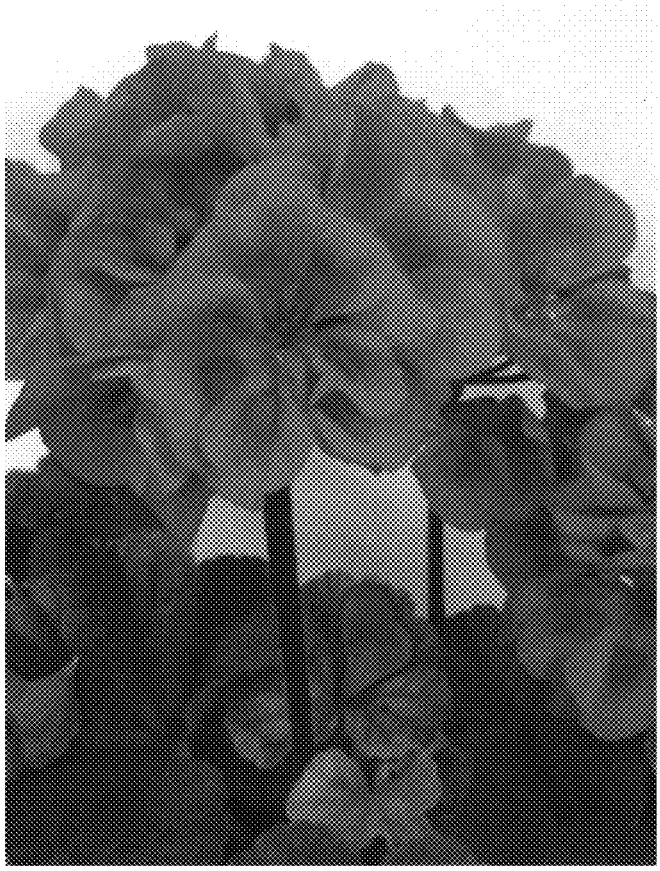

The photographic drawings show in FIG. 1, 1 flowering plant of the new variety and in FIG. 2, a close-up of an inflorescence.

DETAILED BOTANICAL DESCRIPTION

The plant descriptions and measurements were taken in Gilroy, Calif. in early June 2020 under natural light. These plants were approximately 16 weeks old and were grown in a ¼ gallon pots, in a greenhouse trial. The plants shown in the photographs were about 16 weeks old growing in a ¼ gallon inch pot in a greenhouse. The photographs were taken in June 2020.

Color references are made to The Royal Horticultural Society Colour Chart (R.H.S.) 2001.

TABLE 1

DIFFERENCES BETWEEN THE NEW VARIETY 'PECZ0021' AND A MOST SIMILAR VARIETY

| | 'PECZ0021' | 'Clips Rosspla' (U.S. Plant Pat. No. 15,495) |
|---|---|---|
| Color lower surface lower petal: | RHS 63B | More purplish RHS 77D |
| Color lower half upper petal: | RHS 155D; venation, RHS 57A | RHS 46C, striped RHS 46A |

Plant:

*Form, growth and habit.*—Upright, outwardly spreading and rounded growth habit.

*Plant height.*—18-20.0 cm.

*Plant height (inflorescence included).*—28-33.0 cm.

*Plant width.*—28-32.0 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B but whiter.

Foliage:

*Variegation.*—Absent.

*Immature leaf, color upper surface.*—Closest to RHS 137A.

*Immature leaf, lower surface.*—Closest to RHS 137C.

*Mature leaf, color upper surface.*—Closest to RHS 137A.

*Mature leaf, color lower surface.*—Closest to RHS 137C.

*Length.*—6-7 cm.

*Width.*—7-7.5 cm.

*Shape.*—Cordate.

*Base shape.*—Cordate.

*Apex shape.*—Acute.

*Margin.*—Slightly dentate.

*Texture upper side.*—Hirsute.

*Texture lower side.*—Hirsute.

*Leaf zonation color.*—None.

*Color of veins, upper surface.*—RHS 137C becoming indistinct.

*Color of veins, lower surface.*—RHS 137C becoming indistinct.

*Pattern of veining.*—Palmate.

*Petiole color.*—RHS 137C.

*Petiole length.*—5.5-7 cm.

*Diameter of petiole.*—0.2 cm.

*Texture.*—Pilose, hirsute, glandular hairs.

Stem:

*Quantity of branches.*—5-7.

*Color of stem.*—Between RHS 144A and RHS 144B.

*Length of stem.*—10-12.0 cm.

*Diameter.*—0.5 cm.

*Length of internodes.*—1-2 cm.

*Texture.*—Sparsely hirsute, pilose, glandular hairs.

Peduncle:

*Color of peduncle.*—RHS 137C.

*Length of peduncle.*—13-15.0 cm.

*Peduncle diameter.*—0.3-0.35 cm.

*Texture.*—Hirsute, glandular hairs.

Pedicel:

*Color of pedicel.*—Between RHS 187D and RHS 166A.

*Length of pedicel.*—2-3.5 cm.

*Diameter of pedicel.*—0.15-0.2 cm.

*Texture.*—Sparsely pilose, glandular hairs.

Bud (just before opening):

*Color.*—Closest to RHS N66A.

*Length.*—1.5 cm.

*Width.*—0.8-09 cm.

*Shape.*—Elliptical.

Inflorescence:

*Type.*—Umbel; semi-spherical or nearly semi-spherical.

*Lastingness of individual flowers.*—7-9 days at 18° C. temperature.

*Number of inflorescences per plant.*—6, with 6 immature umbels in various stages.

*Fragrance.*—None.

*Umbel diameter.*—9-10 cm.

*Umbel depth.*—6.5-7.5 cm.

Corolla:

*Form.*—Semi-double.

*Number of petals.*—6-7.

*Diameter of flower.*—About 4.5 cm.

*Depth of flower.*—1.3-1.7 cm.

*Color upper petals, upper surface.*—Upper half closest to RHS N66A with darker mottling, RHS 46A, with a spot on the lower half of the petal outer rim RHS 46B, inner RHS 46C, lower half of petal is RHS 46C, striped RHS 46A.

*Color upper petals, lower surface.*—Closest to RHS 46B.

*Length of upper petals.*—2.5 cm.

*Width of upper petals.*—2-2.2 cm.

*Color lower petals, upper surface.*—Upper half to RHS N66A with darker mottling, RHS 46A, with a spot on the lower half of the petal outer rim RHS 46B, inner RHS 46C, lower half of petal is RHS 67C, striped RHS 67A.

*Color lower petals, lower surface.*—Closest to RHS 63B.

*Length of lower petals.*—2.4-2.7 cm.

*Width of lower petals.*—2.3-2.6 cm.

*Petal shape.*—Obovate to spathulate.

*Apex shape.*—Rounded.

*Margin.*—Entire.

*Base.*—Attenuate.

*Petal texture.*—Papillose on both surfaces.

Calyx:

*Number of sepals.*—5.

*Color of sepals.*—RHS 144A mottled with anthocyanins of about RHS 178B.

*Length of sepals.*—1.2 cm.

*Width of sepals.*—0.2-0.4 cm.

*Sepal shape.*—Lanceolate to linear.

*Apex shape.*—Acute.

*Margins.*—Mostly fused.

*Texture, upper surface.*—Glabrous.

*Lower surface.*—Glandular hairs, hirsute.

Reproductive organs:

Gynoecium:

*Pistil.*—1.

*Length.*—1.1 cm.

*Style color*.—Closest to RHS 53A.
*Style length*.—0.5-0.7 cm.
*Stigma color*.—Closest to RHS 53A.
*Ovary color*.—RHS 144A mottled with anthocyanins of about RHS 178B.
*Ovary length*.—0.4-0.5 cm.
*Ovary diameter*.—0.2 cm.

Androecium:

*Number of stamens*.—5-7 with 1-4 staminoids.
*Color of filaments*.—RHS N57B with RHS N155C basally.
*Length filaments*.—0.7-0.8 cm.
*Anther color*.—RHS 51A.
*Length of anthers*.—0.2-0.3 cm.
*Color of pollen*.—Close to N34A.
*Pollen amount*.—Abundant.
*Fertility/seed set*.—Has not been determined to date.
*Disease/pest resistance*.—Has not been determined to date.

What is claimed is:

1. A new and distinct variety of *Pelargonium* plant named 'PECZ0021' substantially as illustrated and described herein.

* * * * *